United States Patent [19]

Muto

[11] 4,094,321
[45] June 13, 1978

[54] SHALLOW, DOME-SHAPED PACER WITH BOTTOM STORAGE MEANS FOR CATHETER

[76] Inventor: Rudolph Muto, 24 Williams St., Andover, Mass. 01810

[21] Appl. No.: 765,888

[22] Filed: Feb. 7, 1977

[51] Int. Cl.² .............................................. A61N 1/02
[52] U.S. Cl. .............................................. 128/419 P
[58] Field of Search ................... 128/404, 405, 419 P, 128/419 PG, 419 PS

[56] References Cited

U.S. PATENT DOCUMENTS

| 3,649,367 | 3/1972 | Purdy | 128/419 P |
| 3,737,579 | 6/1973 | Bolduc | 128/419 P |
| 3,752,162 | 8/1973 | Newash | 128/419 P |
| 3,913,587 | 10/1975 | Newash | 128/419 P |
| 3,938,507 | 2/1976 | Sarnoff et al. | 128/2.06 F |
| 4,013,081 | 3/1977 | Kolenik | 128/419 P |

FOREIGN PATENT DOCUMENTS

| 1,161,578 | 8/1969 | United Kingdom | 128/419 P |
| 507,325 | 4/1976 | U.S.S.R. | 128/419 P |

*Primary Examiner*—William E. Kamm
*Attorney, Agent, or Firm*—Pearson & Pearson

[57] ABSTRACT

To avoid irritation, infection or rejection caused by relatively sharp corner edges, protruding catheter connection heads and squat cylinder shapes of pacemakers implanted in a skin pocket in a human body, a pacemaker of circular outline and shallow, dome-shape with a substantially flat bottom is provided. Catheter storage means is contained in the surface of the flat bottom and comprises a system of helical and radial grooves for releasably receiving any extra length of catheter. The dome-shaped pacer includes a prong socket within its confines and angled toward the bottom grooves and a thrust screw for dislodging the prong.

11 Claims, 8 Drawing Figures

U.S. Patent
June 13, 1978
4,094,321
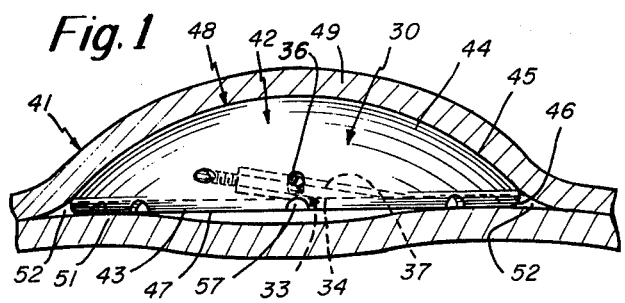
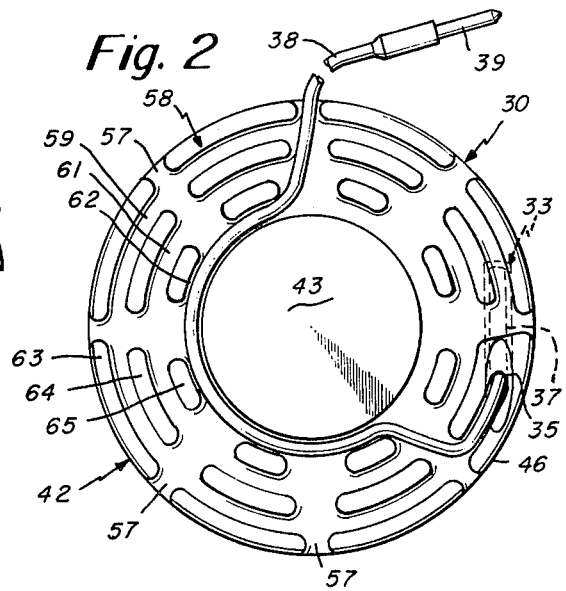
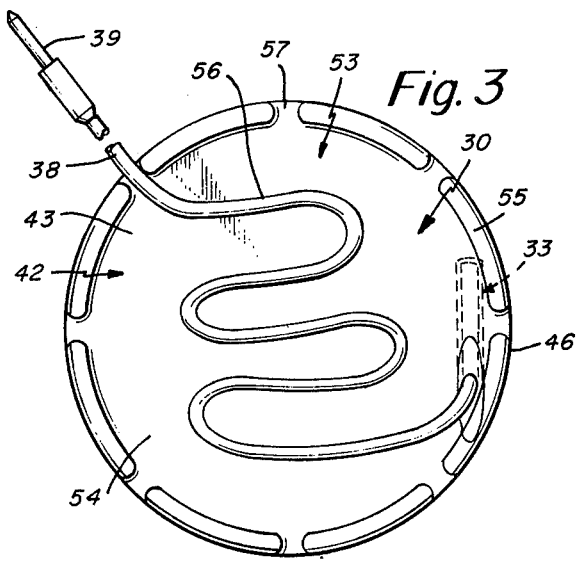
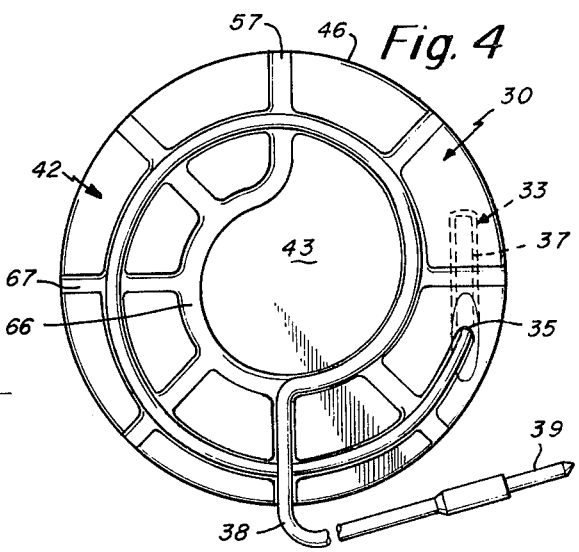
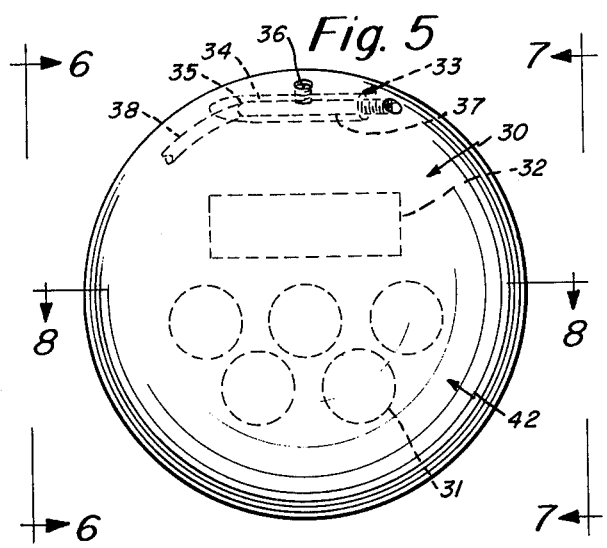
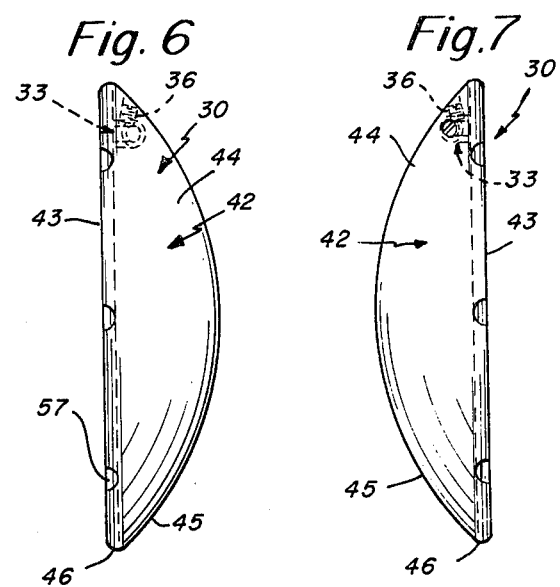
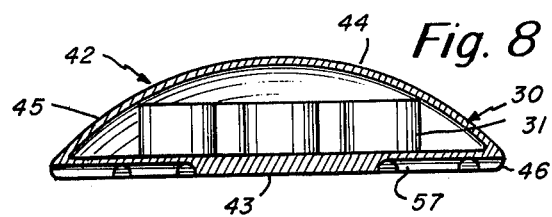

SHALLOW, DOME-SHAPED PACER WITH BOTTOM STORAGE MEANS FOR CATHETER

BACKGROUND OF THE INVENTION

The conventional configuration for heart pacers, and pacemakers has been that of a squat cylinder, or thick disc, with right angular corner edges and a tangentially protruding, catheter connection head. Such pacers are disclosed in U.S. Pat. No. 3,908,668 to Bolduc of Sept. 30, 1975, U.S. Pat. No. 3,918,640 to King of Nov. 11, 1975 and U.S. Pat. No. 3,924,640 to King of Dec. 9, 1975.

It has also been proposed to shape heart pacers in ellipsoid or ovaloid form as in U.S. Pat. No. 3,421,512 to Frasier of Jan. 14, 1969, U.S. Pat. No. 3,866,616 to Purdy of Feb. 18, 1975, U.S. Pat. No. 3,867,950 to Fischell of Feb. 25, 1975 and U.S. Pat. No. 3,987,799 to Purdy of Oct. 26, 1976.

A pacer having a pair of identical, dished, side walls meeting at a sharp edged, central junction is disclosed in FIG. 4 of U.S. Pat. No. 3,957,056 to Comben of May 18, 1976.

The conventional pacemakers, much in use by the medical profession, usually have catheter connection heads which protrude tangentially from circular, thick, cylindrical bodies, centrally of the periphery thereof, and which protruberances may cause infection, irritation or rejection in the skin pocket when implanted in the human body.

In U.S. Pat. No. 3,598,128 to Charduck of Aug. 10. 1971 a cylindrical disc shaped pacer is disclosed in which there is a central groove in the circumferential, or peripheral, edge for releasably receiving an extra length of the catheter, and for rotating the pacer as the body grows. The socket for the prong of the catheter is within the confines of the disc and the device is structurally somewhat similar to a yo-yo.

SUMMARY OF THE INVENTION

In this invention the power supply and pulsation control circuitry of a cardiac pacer is enclosed in a generally dome-shaped casing, the bottom surface being substantially flat and planar and of greater area than the shallow domed top which tapers down to a thin peripheral edge of arcuate cross-section and small radius of curvature juxtaposed to the bottom and merging curvilinearly therewith.

When the dome-shaped, flat bottom pacer is implanted in a pocket under the skin of a patient, the flat bottom seats firmly without tendency to tilt, pivot or rotate and the skin covering the shallow domed top hugs it closely to eliminate any large empty spaces around the peripheral edge in which infection may occur.

The dome-shaped pacer of the invention includes catheter storage means in the surface of the flat bottom, in the form of a pattern of concentric, a helical, continuous grooves, crossed preferably by about eight radially extending grooves, all communicating with each other and of semi-circular cross-section to releasably receive any extra lengths of the catheter lead after implantation. The groove system, or pattern, communicates with the opening of the female socket of the catheter connection element of the pacer, the socket being not only off center towards the flat bottom but also angled toward the plane of the bottom and the element being wholly within the confines of the dome-shaped body rather than protruding therefrom.

In addition the catheter connection element of the pacer of the invention not only has the conventional clamp screw for clamping the prong of the catheter in the socket but also has a thrust screw, operable from outside the pacer and extending coaxially with the socket and prong so that by turning the thrust screw the prong is moved axially out of the socket to dislodge the prong.

BRIEF DESCRIPTION OF THE DRAWING

FIG. 1 is a fragmentary view in section of a part of a human body showing a pacer of the invention implanted in a skin pocket therein;

FIG. 2 is bottom plan view of one embodiment of the groove system in the bottom of a pacer of the invention;

FIG. 3 is a view similar to FIG. 2 showing another embodiment of the catheter storage recess in the bottom of the pacer;

FIG. 4 is a view similar to FIGS. 2 and 3 of the preferred pattern, or system, of grooves in the bottom of the pacer;

FIG. 5 is a top plan view of the dome-shaped pacer of the invention;

FIG. 6 is a side elevation of the pacer of FIG. 5 on line 6—6 of FIG. 5;

FIG. 7 is a side elevation of the pacer of FIG. 5 on line 7—7 of FIG. 5; and

FIG. 8 is a side elevation in section on line 8—8 of FIG. 5.

DESCRIPTION OF A PREFERRED EMBODIMENT

As shown in the drawing, a heart, or cardiac, pacer, or pacemaker, 30 of the invention includes a suitable self-contained power supply 31 and pulsation control circuitry 32 all now well known in the art and disclosed in various forms in the above mentioned patents. The circuitry 32 is connected to the female catheter connection element 33, which includes a socket 34 having an opening 35 and a clamp screw 36, transversely threaded therein, for releasably securing the prong 37 of the catheter lead 38. The catheter lead 38 has a terminal tip 39 which is threaded through a vein to a position in the heart of a human body 41.

The pacer 30 is of generally domical configuration with a hollow casing 42 formed by a substantially flat, planar bottom, or bottom wall, 43 and a shallow domed top, or top wall, 44, the top wall 44 having tapered edges 45 merging in a periphery 46 of arcuate cross-section, and small radius of curvature of about one tenth of an inch, in juxtaposition with the bottom wall 43. Bottom wall 43 has an external surface 47 which may be of metal or may be of epoxy, or any other suitable inert coating used to encapsulate the pacer 30.

As best shown in FIG. 1 the pacer 30 may be implanted in a pocket 48 in the body 41, under the skin 49 and with the flat bottom 43 firmly supported flatwise on muscles or ribs 51 with no tendency to tilt, pivot or rotate in the pocket. The tapered edges 45 and thin periphery 46 of the dome-shaped pacer 30, enable it to hug the skin 49 with a minimum empty space at 52 around the pacer.

Pacer 30 includes catheter storage means 53 in the external surface 47 of the flatbottom 43 which may be a dished recess 54 defined by a peripheral rim 55 into which an extra length, or loop, 56 of the catheter 38 may be festooned as shown in FIG. 3. A plurality of outlets 57 are provided in the rim 55 to enable the surgeon to exit the catheter in any desired quadrant. The catheter loop 56 is held in place after implantation between the bottom wall 43 and the portions 51 of the human body, but the loop is releasably received so that it can be slightly drawn out through its outlet if need be during and after implantation.

As shown in FIG. 2 the catheter storage means is preferably a groove, system, or pattern, 58, which in one form may be a series of concentric grooves 59, 61 and 62 of diminishing radius from the rim 55 toward the center of the surface 47 of bottom 43, and separated by the ribs 63, 64 and 65 of diminishing circumferential length toward the said center. Outlets 57 thus taper toward the outside as shown in avoid sharp bends in the catheter 38. The grooves of the groove system are preferably semi-circular in cross-section and about half the diameter of the catheter 38 in depth.

In FIG. 4 the preferred pattern, or system, 58 of grooves is shown wherein there is single continuous helical groove 66 extending continuously from the opening 35 of the socket 34 circumferentially around the surface 47 of bottom 43 and intersected by the eight radially extending grooves such as 67, each leading to an outlet 57 in the periphery 55.

It will be seen that an extra length, or loop, 56 of catheter 38 may be wound, or seated, in the helical groove 66 to form a path of variable length to any of the radial grooves 67 and outlets 57 and lead from that outlet to the particular position desired in the body 41.

In FIGS. 5, 6, 7 and 8 the preferred embodiment of the pacer 30 is shown as it appears in plan or in edgewise view.

I claim:

1. A heart pacer of the type having a casing with a power supply and pulsation control circuitry therewithin and having a catheter connector socket with a clamp screw operable therein for removably receiving a catheter prong, said pacer characterized by:
a hollow casing of shallow dome configuration, enclosing said power supply and pulsation control circuitry, said casing having a substantially flat, planar, bottom wall and a shallow domed, top wall, said top, domed wall having tapered edges, merging a juxtaposition with the periphery of said flat bottom wall, in an arcuate cross-section of small radius of curvature;
and catheter storage means in the exterior surface of said bottom wall of said casing, for releasably receiving an extra length of said catheter when said pacer is implanted in a human body.

2. A heart pacer as specified in claim 1 wherein:
said catheter storage means is a continuous groove system, said groove system extending from said socket, in a path of variable length, to at least one outlet at said periphery,
whereby said extra length of catheter may be confined in a loop under said pacer and in said groove system without adversely tilting, or pivoting an implanted pacer.

3. A heart pacer as specified in claim 1 wherein:
said catheter storage means comprises a plurality of concentric, grooves extending circumferentially around said surface, and at least one radially extending groove in said surface communicating therewith and extending to an outlet at said periphery.

4. A heart pacer as specified in claim 1 wherein:
said catheter storage means is a continuous helical groove extending therearound, and at least one radial groove intersecting said helical groove and leading to at least one outlet at said periphery said helical groove commencing at said socket.

5. A heart pacer as specified in claim 1:
wherein said catheter storage means comprises grooves extending from said socket in a circumferential and radial pattern and connecting said socket to an outlet at said periphery for receiving a selected extra length of said catheter; and
said socket is substantially wholly within the confines of said domed top wall and angled toward the plane of said bottom wall with the opening of said socket in communication with said grooves.

6. A heart pacer as specified in claim 1 wherein:
said casing includes a thrust screw threaded therein and operable from outside said casing, said thrust screw having a tip normally engaging the prong of the catheter clamped in said head and being arranged to axially dislodge said catheter prong therefrom when said thrust screw is turned.

7. In a heart pacer, for implantation in a human body, of the type having catheter storage means for receiving and releasably storing at least a portion of the length of a catheter, the combination of:
a hollow casing containing the power supply and pulsation control circuitry of said pacer, said casing having a bottom wall of circular substantially flat configuration and a top wall of circular shallow domed configuration said walls merging in a periphery of small radius of cross-section juxtaposed to said bottom wall;
said bottom wall including a pattern of circumferentially extending, and radially extending, continuous communicating grooves, of semi-circular cross-section, said pattern constituting the catheter storage means of said pacer.

8. A heart pacer including a casing having a power supply and pulsation control circuitry therewithin:
said casing being free of corners and protruberances and of generally shallow domed configuration for implantation in a pocket in the human body with minimum unoccupied space therearound;
and said casing having a bottom wall surface with a helical groove formed therein, and at least one radial groove communicating therewith and extending to the periphery of said casing for releasably storing any extra length of the catheter of said pacer.

9. A heart pacer comprising:
a shallow, dome-shaped casing containing the power supply and pulsation control circuitry of said pacer, said casing having a substantially flat bottom and a thin, tapered edge of arcuate cross-section at said bottom;
said bottom having a system of external grooves therein; including a helical groove extending therearound and a plurality of radial grooves communicating with, and crossing, said helical groove for receiving an extra length of loop, of the catheter of said pacer.

10. A heart pacer as specified in claim 9 wherein:
said pacer includes a catheter connection element with a socket angled toward the entrance of said helical groove, said element having a clamp screw threaded transversely therein:

and said element having a thrust screw threaded axially therein for dislodging a catheter prong from said socket.

11. In combination:

a heart pacer of shallow domed configuration, substantially flat bottom and tapered edges;

and catheter storage means in the external surface of said flat bottom, said means including a pattern of grooves, each of semi-circular cross-section, for seating an extra length, or loop, of a catheter when said pacer is implanted in a skin pocket of a human body.

* * * * *